United States Patent
Fukuoka et al.

(10) Patent No.: US 7,812,189 B2
(45) Date of Patent: *Oct. 12, 2010

(54) INDUSTRIAL PROCESS FOR PRODUCTION OF HIGH-PURITY DIPHENYL CARBONATE

(75) Inventors: Shinsuke Fukuoka, Tokyo (JP); Hiroshi Hachiya, Tokyo (JP); Kazuhiko Matsuzaki, Tokyo (JP); Hironori Miyaji, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 719 days.

This patent is subject to a terminal disclaimer.

(21) Appl. No.: 11/660,362

(22) PCT Filed: Aug. 24, 2005

(86) PCT No.: PCT/JP2005/015343

§ 371 (c)(1),
(2), (4) Date: Feb. 16, 2007

(87) PCT Pub. No.: WO2006/022294

PCT Pub. Date: Mar. 2, 2006

(65) Prior Publication Data

US 2008/0041712 A1     Feb. 21, 2008

(30) Foreign Application Priority Data

Aug. 25, 2004 (JP) .......................... 2004-245758

(51) Int. Cl.
C07C 69/96 (2006.01)
(52) U.S. Cl. .................................. 558/270; 558/274
(58) Field of Classification Search ............ 558/270, 558/274
See application file for complete search history.

(56) References Cited

U.S. PATENT DOCUMENTS

| | | | |
|---|---|---|---|
| 4,045,464 A | 8/1977 | Romano et al. | |
| 4,182,726 A | 1/1980 | Illuminati et al. | |
| 4,252,737 A | 2/1981 | Krimm et al. | |
| 4,410,464 A | 10/1983 | Hallgren | |
| 4,552,704 A | 11/1985 | Mark | |
| 4,554,110 A | 11/1985 | Mark | |
| 4,609,501 A | 9/1986 | Mark | |
| 5,210,268 A | 5/1993 | Fukuoka et al. | |
| 5,231,212 A | 7/1993 | Buysch et al. | |
| 5,282,965 A | 2/1994 | Urairi et al. | |
| 5,284,965 A | 2/1994 | Buysch | |
| 5,334,742 A | 8/1994 | Schon et al. | |
| 5,344,954 A | 9/1994 | Schon et al. | |
| 5,359,118 A | 10/1994 | Wagner et al. | |
| 5,362,901 A | 11/1994 | Wagner et al. | |
| 5,426,207 A | 6/1995 | Harrison et al. | |
| 5,495,038 A | 2/1996 | Buysch et al. | |
| 5,705,673 A | 1/1998 | Rivetti et al. | |
| 5,747,609 A | 5/1998 | Komiya et al. | |
| 5,872,275 A | 2/1999 | Komiya et al. | |
| 6,093,842 A | 7/2000 | Oyevaar et al. | |
| 6,197,916 B1 | 3/2001 | Pressman et al. | |
| 6,262,210 B1 * | 7/2001 | Tojo et al. | ........... 526/270 |
| 6,346,638 B1 | 2/2002 | Tojo et al. | |
| 6,479,689 B1 | 11/2002 | Tojo et al. | |
| 6,861,494 B2 | 3/2005 | Debruin | |
| 7,417,161 B2 * | 8/2008 | Woo et al. | ........... 558/270 |
| 7,622,601 B2 * | 11/2009 | Fukuoka et al. | ........... 558/270 |
| 2001/0021786 A1 | 9/2001 | Bruin et al. | |
| 2002/0107355 A1 | 8/2002 | Bouwens et al. | |
| 2004/0236136 A1 | 11/2004 | Schlosberg et al. | |
| 2004/0266974 A1 | 12/2004 | Murthy et al. | |
| 2007/0219387 A1 | 9/2007 | Fukuoka et al. | |
| 2007/0255069 A1 | 11/2007 | Fukuoka et al. | |
| 2007/0260083 A1 | 11/2007 | Fukuoka et al. | |
| 2007/0260084 A1 | 11/2007 | Fukuoka et al. | |
| 2007/0260095 A1 | 11/2007 | Fukuoka et al. | |
| 2007/0265461 A1 | 11/2007 | Fukuoka et al. | |
| 2007/0270604 A1 | 11/2007 | Fukuoka et al. | |
| 2008/0051595 A1 | 2/2008 | Fukuoka et al. | |
| 2008/0064846 A1 | 3/2008 | Fukuoka et al. | |
| 2008/0221348 A1 | 9/2008 | Fukuoka et al. | |
| 2008/0223711 A1 | 9/2008 | Fukuoka et al. | |

FOREIGN PATENT DOCUMENTS

| | | |
|---|---|---|
| DE | 736063 | 6/1943 |
| EA | 010066 | 8/2007 |
| EA | 009715 B1 | 2/2008 |
| EP | 0 461 274 A1 | 12/1991 |
| EP | 0530615 A2 | 3/1993 |
| EP | 0560159 A1 | 9/1993 |
| EP | 0569812 A1 | 11/1993 |
| EP | 0582930 A2 | 2/1994 |
| EP | 0582931 A2 | 2/1994 |
| EP | 0722931 A1 | 7/1996 |

(Continued)

Primary Examiner—Rei-tsang Shiao
(74) Attorney, Agent, or Firm—Birch, Stewart, Kolasch & Birch, LLP (57) ABSTRACT

According to the present invention, there are provided a high boiling point material separating column A and a diphenyl carbonate purifying column B each comprising a continuous multi-stage distillation column having specified structures, and there is provided a specific process that enables a high-purity diphenyl carbonate which is important as a raw material of a high-quality and high-performance polycarbonate to be produced stably for a prolonged period of time on an industrial scale of not less than 1 ton/hr from a reaction mixture containing the diphenyl carbonate using an apparatus in which these two continuous multi-stage distillation columns are connected together.

6 Claims, 1 Drawing Sheet

FOREIGN PATENT DOCUMENTS

| | | |
|---|---|---|
| EP | 0781760 A1 | 7/1997 |
| EP | 0784048 A1 | 7/1997 |
| EP | 0855384 A1 | 7/1998 |
| EP | 0892001 A1 | 1/1999 |
| EP | 1016648 A1 | 7/2000 |
| EP | 1086940 A1 | 3/2001 |
| EP | 1174406 A1 | 1/2002 |
| EP | 1 760 069 A1 | 3/2007 |
| EP | 1762559 A1 | 3/2007 |
| EP | 1762560 A1 | 3/2007 |
| EP | 1767518 | 3/2007 |
| EP | 1 783 112 A1 | 5/2007 |
| EP | 1 787 977 A1 | 5/2007 |
| EP | 1792890 A1 | 6/2007 |
| EP | 1795523 A1 | 6/2007 |
| IT | 1255746 B | 11/1995 |
| JP | 51-75044 | 6/1976 |
| JP | 51-105032 | 9/1976 |
| JP | 54-48732 A | 4/1979 |
| JP | 54-48733 A | 4/1979 |
| JP | 54-63023 A | 5/1979 |
| JP | 56-25138 A | 3/1981 |
| JP | 56-123948 A | 9/1981 |
| JP | 56-123949 A | 9/1981 |
| JP | 57-176932 A | 10/1982 |
| JP | 57-183745 A | 11/1982 |
| JP | 58-185536 A | 10/1983 |
| JP | 60-169444 A | 9/1985 |
| JP | 60-169445 A | 9/1985 |
| JP | 60-173016 A | 9/1985 |
| JP | 61-172852 A | 8/1986 |
| JP | 61-291545 A | 12/1986 |
| JP | 62-277345 A | 12/1987 |
| JP | 1-93560 A | 4/1989 |
| JP | 1-265062 A | 10/1989 |
| JP | 1-265063 A | 10/1989 |
| JP | 1-265064 A | 10/1989 |
| JP | 3-291257 A | 12/1991 |
| JP | 4-9358 A | 1/1992 |
| JP | 4-100824 A | 4/1992 |
| JP | 4-198141 A | 7/1992 |
| JP | 4-211038 A | 8/1992 |
| JP | 4-224547 A | 8/1992 |
| JP | 4-230242 A | 8/1992 |
| JP | 4-235951 A | 8/1992 |
| JP | 5-213830 A | 8/1993 |
| JP | 6-9506 A | 1/1994 |
| JP | 6-9507 A | 1/1994 |
| JP | 6-41022 A | 2/1994 |
| JP | 6-157424 A | 6/1994 |
| JP | 6-184058 A | 7/1994 |
| JP | 7-101908 A | 4/1995 |
| JP | 7-304713 A | 11/1995 |
| JP | 9-40616 A | 2/1997 |
| JP | 9-59224 A | 3/1997 |
| JP | 9-59225 A | 3/1997 |
| JP | 9-110805 A | 4/1997 |
| JP | 9-165357 A | 6/1997 |
| JP | 9-169704 A | 6/1997 |
| JP | 9-173819 A | 7/1997 |
| JP | 9-176094 A | 7/1997 |
| JP | 9-194435 A | 7/1997 |
| JP | 9-194436 A | 7/1997 |
| JP | 9-194437 A | 7/1997 |
| JP | 9-255772 A | 9/1997 |
| JP | 10-245366 A | 9/1998 |
| JP | 11-12230 A | 1/1999 |
| JP | 11-49727 A | 2/1999 |
| JP | 11-92429 A | 4/1999 |
| JP | 11-228504 A | 8/1999 |
| JP | 2000-191596 A | 7/2000 |
| JP | 2000-191597 A | 7/2000 |
| JP | 2001-64234 A | 3/2001 |
| JP | 2001-64235 A | 3/2001 |
| JP | 2003-113144 A | 4/2003 |
| JP | 2003-119168 A | 4/2003 |
| JP | 2003-155264 A | 5/2003 |
| JP | 2003-516376 A | 5/2003 |
| JP | 2003-300936 A | 10/2003 |
| JP | 2003-342209 A | 12/2003 |
| JP | 2004-131421 A | 4/2004 |
| JP | 2004-323384 A | 11/2004 |
| JP | 2006-182683 A | 7/2006 |
| JP | 2006-199643 A | 8/2006 |
| JP | 2006-206497 A | 8/2006 |
| RU | 2 041 869 C1 | 8/1995 |
| WO | WO-91/09832 A1 | 7/1991 |
| WO | WO-92/18458 A1 | 10/1992 |
| WO | WO-97/11049 A1 | 3/1997 |
| WO | WO-99/64382 A1 | 12/1999 |
| WO | WO-99/64492 A1 | 12/1999 |
| WO | WO-00/18720 A1 | 4/2000 |
| WO | WO-00/51954 A1 | 9/2000 |
| WO | WO-01/42187 A1 | 6/2001 |
| WO | WO-02/40439 A2 | 5/2002 |
| WO | WO-03/016257 A1 | 2/2003 |
| WO | WO03/066569 * | 8/2003 |
| WO | WO-2005/123638 A1 | 12/2005 |
| WO | WO-2006/001256 A1 | 1/2006 |
| WO | WO-2006/022294 A1 | 3/2006 |
| WO | WO-2006/025424 A1 | 3/2006 |
| WO | WO-2006-025478 A | 3/2006 |
| WO | WO-2006/041075 A1 | 4/2006 |

* cited by examiner

FIG.1

INDUSTRIAL PROCESS FOR PRODUCTION OF HIGH-PURITY DIPHENYL CARBONATE

TECHNICAL FIELD

The present invention relates to an industrial process for the production of a high-purity diphenyl carbonate. More particularly, the present invention relates to an industrial process for the production of a high-purity diphenyl carbonate, which is useful as a raw material of a transesterification method polycarbonate, by using two continuous multi-stage distillation columns having specified structures, from a reaction mixture containing a diphenyl carbonate obtained by carrying out a transesterification reaction between a dialkyl carbonate and a phenol and/or a disproportionation reaction of an alkyl phenyl carbonate and/or a transesterification reaction between an alkyl phenyl carbonate and a phenol.

BACKGROUND ART

A high-purity diphenyl carbonate is important as a raw material for the production of an aromatic polycarbonate, which is the most widely used engineering plastics, without using toxic phosgene. As a process for producing an aromatic carbonate, a process of reacting an aromatic monohydroxy compound with phosgene has been known from long ago, and has also been the subject of a variety of studies in recent years. However, this process has the problem of using phosgene, and in addition chlorinated impurities that are difficult to separate out are present in the aromatic carbonate produced using this process, and hence this aromatic carbonate cannot be used as a raw material for the production of the aromatic polycarbonate. Because such chlorinated impurities markedly inhibit the polymerization reaction in the transesterification method which is carried out in the presence of an extremely small amount of a basic catalyst; for example, even if such chlorinated impurities are present in an amount of only 1 ppm, the polymerization hardly proceeds at all. To make the aromatic carbonate capable of using as a raw material of a transesterification method polycarbonate, a troublesome multi-stage separation/purification processes such as enough washing with a dilute aqueous alkaline solution and hot water, oil/water separation, distillation and so on are thus required. Furthermore, the yield of aromatic carbonate decreases due to hydrolysis loss and distillation loss during this separation/purification processes. Therefore, there are many problems in carrying out this method economically on an industrial scale.

On the other hand, a process for producing aromatic carbonates through transesterification reactions between dialkyl carbonates and aromatic monohydroxy compounds are also known. However, such transesterification reactions are all equilibrium reactions. Since the equilibriums are biased extremely toward the original system and the reaction rates are slow, there have been many difficulties in producing the aromatic carbonate industrially in large amounts using this method. Two types of proposals have been made to improve on the above difficulties. One of these relates to development of a catalyst to increase the reaction rate, and many metal compounds have been proposed as the catalyst for the above type of the transesterification reactions. For example, Lewis acids such as transition metal halides and Lewis acid-forming compounds (see Patent Documents 1: Japanese Patent Application Laid-Open No. 51-105032, Japanese Patent Application Laid-Open No. 56-123948, Japanese Patent Application Laid-Open No. 56-123949 (corresponding to West German Patent Application No. 2528412, British Patent No. 1499530, and U.S. Pat. No. 4,182,726), Japanese Patent Application Laid-Open No. 51-75044 (corresponding to West German Patent Application No. 2552907, and U.S. Pat. No. 4,045,464)), tin compounds such as organotin alkoxides and organotin oxides (see Patent Documents 2: Japanese Patent Application Laid-Open No. 54-48733 (corresponding to West German Patent Application No. 2736062), Japanese Patent Application Laid-Open No. 54-63023, Japanese Patent Application Laid-Open No. 60-169444 (corresponding to U.S. Pat. No. 4,554,110), Japanese Patent Application Laid-Open No. 60-169445 (corresponding to U.S. Pat. No. 4,552,704), Japanese Patent Application Laid-Open No. 62-277345, Japanese Patent Application Laid-Open No. 1-265063), salts and alkoxides of alkali metals and alkaline earth metals (see Patent Document 3: Japanese Patent Application Laid-Open No. 57-176932), lead compounds (see Patent Documents 4: Japanese Patent Application Laid-Open No. 57-176932, Japanese Patent Application Laid-Open No. 1-93560), complexes of metals such as copper, iron and zirconium (see Patent Document 5: Japanese Patent Application Laid-Open No. 57-183745), titanic acid esters (see Patent Documents 6: Japanese Patent Application Laid-Open No. 58-185536 (corresponding to U.S. Pat. No. 4,410,464), Japanese Patent Application Laid-Open No. 1-265062), mixtures of a Lewis acid and protonic acid (see Patent Document 7: Japanese Patent Application Laid-Open No. 60-173016 (corresponding to U.S. Pat. No. 4,609,501)), compounds of Sc, Mo, Mn, Bi, Te or the like (see Patent Documents 8: Japanese Patent Application Laid-Open No. 1-265064), ferric acetate (see Patent Document 9: Japanese Patent Application Laid-Open No. 61-172852), and so on have been proposed.

Since the problem of the disadvantageous equilibrium cannot be solved merely by developing the catalyst, as the other type of the proposals, attempts have been made to devise a reaction system so as to shift the equilibrium toward the product system as much as possible, thus improving the aromatic carbonate yield. For example, for the reaction between dimethyl carbonate and phenol, there have been proposed a method in which methanol produced as a by-product is distilled off by azeotropy together with an azeotrope-forming agent (see Patent Documents 10: Japanese Patent Application Laid-Open No. 54-48732 (corresponding to West German Patent Application No. 736063, and U.S. Pat. No. 4,252,737)), and a method in which the methanol produced as a by-product is removed by being adsorbed onto a molecular sieve (see Patent Documents 11: Japanese Patent Application Laid-Open No. 58-185536 (corresponding to U.S. Pat. No. 410,464)). Moreover, a method has also been proposed in which, using an apparatus in which a distillation column is provided on top of a reactor, an alcohol produced as a by-product in the reaction is separated off from the reaction mixture, and at the same time an unreacted starting material that evaporates is separated off by distillation (see Patent Documents 12: examples in Japanese Patent Application Laid-Open No. 56-123948 (corresponding to U.S. Pat. No. 4,182,726), examples in Japanese Patent Application Laid-Open No. 56-25138, examples in Japanese Patent Application Laid-Open No. 60-169444 (corresponding to U.S. Pat. No. 4,554,110), examples in Japanese Patent Application Laid-Open No. 60-169445 (corresponding to U.S. Pat. No. 4,552,704), examples in Japanese Patent Application Laid-Open No. 60-173016 (corresponding to U.S. Pat. No. 4,609,501), examples in Japanese Patent Application Laid-Open No. 61-172852, examples in Japanese Patent Application Laid-Open No. 61-291545, examples in Japanese Patent Application Laid-Open No. 62-277345).

However, these reaction systems have basically been batch system or switchover system. Because there are limitations in the improvement of the reaction rate through catalyst development for such transesterification reactions, and the reaction rates are still slow, and thus it has been thought that the batch system is preferable to a continuous system. Of these, a continuous stirring tank reactor (CSTR) system in which a distillation column is provided on the top of the reactor has been proposed as the continuous system, but there are problems such as the reaction rate being slow, and a gas-liquid interface in the reactor being small, based on the volume of the liquid. Hence it is not possible to make the reaction ratio high. Accordingly, it is difficult to attain the object of producing the aromatic carbonate continuously in large amounts stably for a prolonged period of time by means of the above-mentioned methods, and many issues remain to be resolved before economical industrial implementation is possible.

The present inventors have developed reactive distillation methods in which such a transesterification reaction is carried out in a continuous multi-stage distillation column simultaneously with separation by distillation, and have been the first in the world to disclose that such a reactive distillation system is useful for such a transesterification reaction, for example, a reactive distillation method in which a dialkyl carbonate and an aromatic hydroxy compound are continuously fed into the multi-stage distillation column, and the reaction is carried out continuously inside the column in which a catalyst is present, while continuously withdrawing a low boiling point component containing an alcohol produced as a by-product by distillation and continuously withdrawing a component containing a produced alkyl aryl carbonate from a lower portion of the column (see Patent Document 13: Japanese Patent Application Laid-Open No. 3-291257), a reactive distillation method in which an alkyl aryl carbonate is continuously fed into the multi-stage distillation column, and the reaction is carried out continuously inside the column in which a catalyst is present, while continuously withdrawing a low boiling point component containing a dialkyl carbonate produced as a by-product by distillation, and continuously withdrawing a component containing a produced diaryl carbonate from a lower portion of the column (see Patent document 14: Japanese Patent Application Laid-Open No. 4-9358), a reactive distillation method in which these reactions are carried out using two continuous multi-stage distillation columns, and hence a diaryl carbonate is produced continuously while efficiently recycling a dialkyl carbonate produced as a by-product (see Patent document 15: Japanese Patent Application Laid-Open No. 4-211038), and a reactive distillation method in which a dialkyl carbonate and an aromatic hydroxy compound or the like are continuously fed into the multi-stage distillation column, and a liquid that flows down through the column is withdrawn from a side outlet provided at an intermediate stage and/or a lowermost stage of the distillation column, and is introduced into a reactor provided outside the distillation column so as to bring about reaction, and is then introduced back through a circulating inlet provided at a stage above the stage where the outlet is provided, whereby reaction is carried out in both the reactor and the distillation column (see Patent Documents 16: Japanese Patent Application Laid-Open No. 4-224547, Japanese Patent Application Laid-Open No. 4-230242, Japanese Patent Application Laid-Open No. 4-235951).

These reactive distillation methods proposed by the present inventors are the first to enable aromatic carbonates to be produced continuously and efficiently, and many similar reactive distillation systems based on the above disclosures have been proposed thereafter (see Patent Documents 17 to 32: Patent Document 17: International Publication No. 00/18720 (corresponding to U.S. Pat. No. 5,362,901), Patent Document 18: Italian Patent No. 01255746, Patent Document 19: Japanese Patent Application Laid-Open No. 6-9506 (corresponding to European Patent No. 0560159, and U.S. Pat. No. 5,282,965), Patent Document 20: Japanese Patent Application Laid-Open No. 6A41022 (corresponding to European Patent No. 0572870, and U.S. Pat. No. 5,362,901), Patent Documents 21: Japanese Patent Application Laid-Open No. 6-157424 (corresponding to European Patent No. 0582931, and U.S. Pat. No. 5,334,742), Japanese Patent Application Laid-Open No. 6-184058 (corresponding to European Patent No. 0582930, and U.S. Pat. No. 5,344,954), Patent Document 22: Japanese Patent Application Laid-Open No. 7-304713, Patent Document 23': Japanese Patent Application Laid-Open No. 940616, Patent Document 24: Japanese Patent Application Laid-Open No. 9-59225, Patent Document 25: Japanese Patent Application Laid-Open No. 9-110805, Patent Document 26: Japanese Patent Application Laid-Open No. 9-165357, Patent Document 27: Japanese Patent Application Laid-Open No. 9-173819, Patent Documents 28: Japanese Patent Application Laid-Open No. 9-176094, Japanese Patent Application Laid-Open No. 2000-191596, Japanese Patent Application Laid-Open No. 2000-191597, Patent Documents 29: Japanese Patent Application Laid-Open No. 9-194436 (corresponding to European Patent No. 0785184, and U.S. Pat. No. 5,705,673), Patent Documents 30: International Publication No. 00/18720 (corresponding to U.S. Pat. No. 6,093, 842), International Publication No. 01/042187 (corresponding to Published Japanese Translation of PCT Application No. 2003-516376), Patent Documents 31: Japanese Patent Application Laid-Open No. 2001-64234, Japanese Patent Application Laid-Open No. 2001-64235, Patent Document 32: International Publication No. 02/40439 (corresponding to U.S. Pat. No. 6,596,894, U.S. Pat. No. 6,596,895, and U.S. Pat. No. 6,600,061)).

Among the reactive distillation systems, the present applicants have further proposed, as a method that enables highly pure aromatic carbonates to be produced stably for a prolonged period of time without a large amount of a catalyst being required, a method in which a high boiling point material containing a catalyst component is reacted with a n active substance and then separated off, and the catalyst component is recycled (see Pa tent Documents 33: International Publication No. 97/11049 (corresponding to European Patent No. 0855384, and U.S. Pat. No. 5,872,275)), and a method carried out while keeping the weight ratio of a polyhydric aromatic hydroxy compound in the reaction system to a catalyst metal at not more than 2.0 (see Patent Documents 34: Japanese Patent Application Laid-Open No. 11-92429 (corresponding to European Patent No. 1016648, and U.S. Pat. No. 6,262, 210)). Furthermore, the present inventors have also proposed a method in which 70 to 99% by weight of phenol produced as a by-product in a polymerization process is used as a starting material, and diphenyl carbonate can be produced by means of the reactive distillation method. This diphenyl carbonate can be used as the raw material for polymerization to produce aromatic polycarbonates (see Patent Documents 35: Japanese Patent Application Laid-Open No. 9-255772 (corresponding to European Patent No. 0892001, and U.S. Pat. No. 5,747,609)).

However, in all of these prior art documents in which the production of the aromatic carbonates using the reactive distillation method is proposed, there is no disclosure whatsoever of a specific process or apparatus enabling mass production on an industrial scale (e.g. more than 1 ton per hr), nor is there any description suggesting such a process or apparatus. For example, the descriptions regarding heights ($H_1$ and $H_2$: cm), diameters ($D_1$ and $D_2$: cm), the numbers of stages ($N_1$ and $N_2$), and the feeding rates of the raw materials ($Q_1$ and $Q_2$: kg/hr) for two reactive distillation columns disclosed for producing mainly diphenyl carbonate (DPC) from dimethyl carbonate and phenol are as summarized in the following table.

TABLE 1

| $H_1$ | $D_1$ | $N_1$ | $Q_1$ | $H_2$ | $D_2$ | $N_2$ | $Q_2$ | PATENT DOCUMENT |
|---|---|---|---|---|---|---|---|---|
| 600 | 25 | 20 | 66 | 600 | 25 | 20 | 23 | 15 |
| 350 | 2.8 | — | 0.2 | 305 | 5~10 | 15 + PACKING | 0.6 | 21 |
| 500 | 5 | 50 | 0.6 | 400 | 8 | 50 | 0.6 | 23 |
| 100 | 4 | — | 1.4 | 200 | 4 | — | 0.8 | 24 |
| 300 | 5 | 40 | 1.5 | — | 5 | 25 | 0.7 | 28 |
| 1200 | 20 | 40 | 86 | 600 | 25 | 20 | 31 | 33 34 |
| 600 | — | 20 | 66 | 600 | — | 20 | 22 | 35 |

In other words, the biggest continuous multi-stage distillation columns used when carrying out this reaction using the reactive distillation system are those disclosed by the present applicants in Patent Documents 33 and 34. As can be seen from Table 1, the maximum values of the various conditions for the continuous multi-stage distillation columns disclosed for the above reaction are $H_1$=1200 cm, $H_2$=600 cm, $D_1$=20 cm, $D_2$=25 cm, $N_1$=$N_2$=50 (Patent Document 25), $Q_1$=86 kg/hr, and $Q_2$=31 kg/hr, and the total amount of diphenyl carbonate produced was only approximately 6.7 kg/hr, which was not an amount produced on an industrial scale.

As methods for separating the diphenyl carbonate from the reaction mixture containing a diphenyl carbonate that has been produced through transesterification reaction and the like between a dialkyl carbonate and a phenol as a starting material as described above, and then purifying the diphenyl carbonate, crystallization methods, distillation methods and the like have been proposed. With regard to the distillation methods, three methods have been proposed. One is a method in which the diphenyl carbonate is obtained as a column top component from a distillation column; for example, there are:

I) a method in which the reaction mixture containing the catalyst is distilled as is in a batch type distillation column, and the diphenyl carbonate is obtained as the column top component (see example of Patent Document 10, example 2 of Patent Document 19);

II) a method in which the reaction mixture containing the catalyst is subjected to flash evaporation, and thus separated into a high boiling point material containing most of the catalyst and a low boiling point material, and then the low boiling point material is distilled in a distillation column for starting material recovery, and a catalyst-containing diphenyl carbonate is obtained as a column bottom material, and then this column bottom material is distilled in a purifying column, whereby the diphenyl carbonate is obtained as a column top component (see Patent Document 37: example 1 in Japanese Patent Application Laid-open No. 4-100824, Patent Document 38: Japanese Patent Application Laid-open No. 9-169704); and III) a method in which the reaction mixture containing the catalyst is distilled in a distillation column (or evaporator), and thus separated into a high boiling point material containing most of the catalyst and a low boiling point material, and then the low boiling point material is subjected to continuous sequential distillation using a distillation apparatus comprising three columns, i.e. a light fraction separating column, a methyl phenyl carbonate separating column, and a diphenyl carbonate separating column, whereby diphenyl carbonate is obtained as a column top component (see Patent Document 25).

Another is a method in which the diphenyl carbonate is obtained as a column bottom component from a distillation column; for example, there is:

IV) a method in which the reaction mixture containing the catalyst is distilled in a distillation column, and thus separated into a high boiling point material containing most of the catalyst and a low boiling point material, and then the low boiling point material is distilled in a distillation column, and the diphenyl carbonate is obtained as a column bottom component (see Patent Document 31).

The other is a method in which the diphenyl carbonate is obtained as a side cut component from a distillation column; for example, there are:

V) a method in which the reaction mixture containing the catalyst is introduced into a third reactive distillation column, and further reaction and distillation are carried out, whereby the diphenyl carbonate is obtained as a side cut component from the reactive distillation column (see Patent Document 21);

VI) a method in which the reaction mixture containing the catalyst is subjected to flash evaporation, and thus separated into a high boiling point material containing most of the catalyst and a low boiling point material, and then the low boiling point material is introduced into a distillation column and distillation is carried out, whereby the diphenyl carbonate is obtained as a side cut component from the reactive distillation column (see Patent Documents 34 and 35, Patent Document 39: International Publication No. 92/18458 (corresponding to U.S. Pat. No. 5,426,207);

VII) a method in which the reaction mixture containing the catalyst is distilled in a first purifying column, and thus separated into a high boiling point material containing most of the catalyst and a low boiling point material, and then the low boiling point material is introduced into a second purifying column and distillation is carried out, whereby the diphenyl carbonate is obtained as a side cut component from the second purifying column (see Patent Document 40: Japanese Patent Application Laid-open No. 11-49727); and VIII) a method in which diphenyl carbonate containing phenyl salicylate is introduced into a distillation column having the number of theoretical stages being from 5 to 15, and distillation is carried out at a column bottom temperature of not less than 150° C., whereby the diphenyl carbonate is obtained as a side cut component from the distillation column (see Patent Document 36: Japanese Patent Application Laid-open No. 9-194437 (corresponding to European Patent No. 0784048)).

However, it has been shown that various problems remain with such diphenyl carbonate separation/purification methods using these distillations. More specifically, the purity of the diphenyl carbonate obtained through the above I) is low, and moreover this is a batch process and hence is not suitable for mass production on an industrial scale. Regarding the above II), the method of Patent Document 37 is a batch method, and the diphenyl carbonate which was obtained through the method disclosed in Patent Document 38 contains a titanium catalyst, albeit in an amount of not more than 1 ppm, and hence is not suitable as a raw material for the production of a high-purity discolored polycarbonate. With the method of the above III), since the diphenyl carbonate is heated to a high temperature at the bottom of each of two of the distillation columns, i.e. the light fraction separating column and the methyl phenyl carbonate separating column, and is then subjected to a high temperature in the diphenyl carbonate separating column, the diphenyl carbonate is altered, bringing about a decrease in the purity and a decrease in the yield.

Moreover, the method of the above IV) in which the diphenyl carbonate is obtained from the column bottom is unsuitable, because the purity is low and hence a desired polycarbonate cannot be produced.

With the method of the above V), the reaction mixture containing the catalyst, the unreacted starting material and the impurities obtained from the bottom of the second reactive distillation column is introduced into the third reactive distillation column from an upper portion thereof, and the diphenyl carbonate is withdrawn from the side of the third reactive distillation column. Vapor or mist of the catalyst, the starting material, the impurities and the like may thus be entrained, and hence the purity of the diphenyl carbonate is low. With the method of the above VI), the amount of diphenyl carbonate produced is 6.7 kg/hr (example 3 of Patent Document 34) or 3.9 kg/hr (example 1 of Patent Document 35), which is not on an industrial scale. The method of the above VII) is a preferable process, but the amount of diphenyl carbonate produced is small at 2 kg/hr (example 8 of Patent Document 40), which is not on an industrial scale. Moreover, the method is carried out with the column top pressure in the first purifying column at a high vacuum of 200 Pa, and hence industrial implementation would be difficult, because a very large distillation column would be required so that the high vacuum could be maintained.

Moreover, with the method of the above VIII), although it is stated that the content of phenyl salicylate is reduced from 3000 ppm to 50 ppm (example 2 of Patent Document 36), nothing is stated whatsoever for other impurities. For example, even though the diphenyl carbonate is produced using the phosgene method in this example, and hence this is definitely a purification method for diphenyl carbonate containing chlorinated impurities, nothing is stated whatsoever with regard to the chlorinated impurities (which have an adverse effect on the polymerization to produce a polycarbonate and the properties of the polycarbonate even in an extremely small amount of only a few tens of ppb). With this method, such chlorinated impurities will not be separated out sufficiently, and hence it will not be possible to use the diphenyl carbonate as a raw material for a polycarbonate. This is as described in comparative example 1 (in which the alkali column is not used) of the purification method (in which after washing twice with alkaline hot water, washing with hot water is carried out, and then the diphenyl carbonate is dehydrated through distillation and then passed through a column filled with a solid alkali, before being subjected to reduced pressure distillation in the multi-stage distillation column) of Patent Document 41 (Japanese Patent Application Laid-Open No. 9-194437), which was filed more than one year after the filing of Patent Document 36.

Furthermore, in Patent Document 36, the temperature and time at which phenol starts to be distilled off in the case that reaction is carried out with bisphenol A are given as a method of evaluating the purity of the diphenyl carbonate obtained through the distillation, but evaluation of whether the diphenyl carbonate is suitable for polymerization cannot be carried out using this test method. This is because even for diphenyl carbonate of low purity such that a polycarbonate of the required degree of polymerization cannot be produced, the initial reaction in which phenol is eliminated occurs sufficiently. Moreover, since with this evaluation method, a large amount of 2.3 ppm of NaOH based on the bisphenol A is used as a catalyst, even for diphenyl carbonate containing, for example, 1 ppm of chlorinated impurities, an incorrect evaluation that the diphenyl carbonate is of high purity and is suitable as a raw material for a polycarbonate would be obtained. As stated earlier, the diphenyl carbonate containing 1 ppm of chlorinated impurities cannot be used as the raw material for the polycarbonate at all. In ordinary polymerization, since such a large amount of an alkaline catalyst is not used, this evaluation method is not suitable for evaluating the purity of diphenyl carbonate to be used for producing polycarbonate. Further, in Patent Document 36, there is no specific description whatsoever of purification of diphenyl carbonate that has been obtained using the transesterification method. Since the types and contents of impurities differ between diphenyl carbonate obtained through the phosgene method and diphenyl carbonate obtained using the transesterification method, it cannot be said that diphenyl carbonate of the same purity will be obtained through the same purification method. It thus cannot be said at all that diphenyl carbonate having the required purity for the raw material of the polycarbonate would be obtained through the purification method of Patent Document 36. Furthermore, the amount of purified diphenyl carbonate disclosed in Patent Document 36 is 0.57 kg/hr, which is not on an industrial scale.

A reaction mixture obtained through transesterification reaction between a dialkyl carbonate and a phenol as a starting material in the presence of a homogeneous catalyst generally contains various reaction by-products. In particular, if a diphenyl carbonate containing the amounts of high boiling point by-products having a higher boiling point than that of the diphenyl carbonate, such as phenyl salicylate, xanthone, phenyl methoxybenzoate, 1-phenoxycarbonyl-2-phenoxycarboxy-phenylene and the like which have not been reduced down to a sufficient level is used as the raw material of the transesterification method polycarbonate, then these high boiling point by-products will cause coloration and deterioration in properties. It is thus preferable to reduce the amounts of such impurities as much as possible. However, such high boiling point by-products are difficult to separate out, and with methods proposed hitherto, it has not been possible to reduce the amounts of such high boiling point by-products down to a sufficient level. In particular, there has been no proposal whatsoever of a process for the production on an industrial scale of not less than 1 ton/hr of a high-purity diphenyl carbonate required for the raw material of a high-quality and high-performance polycarbonate.

DISCLOSURE OF INVENTION

It is an object of the present invention to provide a specific process that enables a high-purity diphenyl carbonate that can be used as a raw material of a high-quality and high-performance polycarbonate to be produced stably for a prolonged period of time on an industrial scale of not less than 1 ton/hr from a reaction mixture containing a catalyst and reaction by-products that has been obtained through transesterification reaction and the like using a dialkyl carbonate and a phenol as a starting material.

Since the present inventors disclosed a process for producing aromatic carbonates using the continuous multi-stage distillation column, various proposals regarding processes for the production of reaction mixtures containing aromatic carbonates by means of the reactive distillation method have been made. However, these have all been on a small scale and a short operating time laboratory level, and there have been no disclosures on a specific process or apparatus enabling mass production on an industrial scale from such a reaction mixture to a high-purity diphenyl carbonate that can be used as the raw material of a high-quality and high-performance polycarbonate. In view of these circumstances, the present inventors carried out studies aimed at discovering a specific process enabling a high-purity diphenyl carbonate which is important as the raw material of the high-quality and high-performance polycarbonate to be produced stably for a prolonged period of time on an industrial scale of not less than 1 ton/hr. As a result, the present inventors have reached to the present invention.

That is, in the first aspect of the present invention, there is provided:

1. In an industrial process for the production of a high-purity diphenyl carbonate which is produced continuously from a reaction mixture containing a diphenyl carbonate, which has been obtained by carrying out a transesterification reaction between a dialkyl carbonate and a phenol and/or a disproportionation reaction of an alkyl phenyl carbonate and/or a transesterification reaction between an alkyl phenyl carbonate and a phenol in the presence of a homogeneous catalyst, by continuously introducing said reaction mixture into a high boiling point material separating column A, and continuously carrying out separation by distillation into a column top component $A_T$ containing the diphenyl carbonate and a column bottom component $A_B$ containing the catalyst, and then continuously introducing said column top component $A_T$ into a diphenyl carbonate purifying column B having a side cut outlet, and continuously carrying out separation by distillation into a column top component $B_T$, a side cut component $B_S$ and a column bottom component $B_B$, the improvement which comprises:

(a) said high boiling point material separating column A comprises a continuous multi-stage distillation column having a length $L_A$ (cm), an inside diameter $D_A$ (cm), and an internal with a number of stages $n_A$ thereinside, wherein $L_A$, $D_A$, and $n_A$ satisfy the following formulae (1) to (3);

$$800 \leq L_A \leq 3000 \quad (1)$$

$$100 \leq D_A \leq 1000 \quad (2)$$

$$20 \leq n_A \leq 100 \quad (3);$$

(b) a distillation operation of said high boiling point material separating column A is carried out under conditions of a column bottom temperature $T_A$ in a range of from 185 to 280° C., and a column top pressure $P_A$ in a range of from 1000 to 20000 Pa;

(c) said diphenyl carbonate purifying column B comprises a continuous multi-stage distillation column having a length $L_B$ (cm), an inside diameter $D_B$ (cm), an internal thereinside, an inlet B1 at a middle portion of the column, and a side cut outlet B2 between said inlet B1 and the column bottom, in which a number of stages of the internal above the inlet B1 is $n_1$, a number of stages of the internal between the inlet B1 and the side cut outlet B2 is $n_2$, a number of stages of the internals below the side cut outlet B2 is $n_3$, and a total number of stages is $n_B$ (=$n_1+n_2+n_3$), wherein $L_B$, $D_B$, $n_1$, $n_2$, $n_3$, and $n_B$ satisfy the following formulae (4) to (9);

$$1000 \leq L_B \leq 5000 \quad (4)$$

$$100 \leq D_B \leq 1000 \quad (5)$$

$$5 \leq n_1 \leq 20 \quad (6)$$

$$12 \leq n_2 \leq 40 \quad (7)$$

$$3 \leq n_3 \leq 15 \quad (8)$$

$$20 \leq n_B \leq 70 \quad (9);$$

(d) a distillation operation of said diphenyl carbonate purifying column B is carried out under conditions of a column bottom temperature $T_B$ in a range of from 185 to 280° C., and a column top pressure $P_B$ in a range of from 1000 to 20000 Pa; and (e) not less than 1 ton/hr of the high-purity diphenyl carbonate is obtained continuously as the side cut component $B_S$.

2. The process according to item 1, wherein $L_A$, $D_A$, and $n_A$ for said high boiling point material separating column A satisfy the following formulae: $1000 \leq L_A \leq 2500$, $200 \leq D_A \leq 600$, and $30 \leq n_A \leq 70$, respectively, $L_B$, $D_B$, $n_1$, $n_2$, $n_3$, and $n_B$ for said diphenyl carbonate purifying column B satisfy the following formulae: $1500 \leq L_B \leq 3000$, $150 \leq D_B \leq 500$, $7 \leq n_1 \leq 15$, $12 \leq n_2 \leq 30$, $3 \leq n_3 \leq 10$, and $25 \leq n_B \leq 55$, respectively, $T_A$ is in a range of from 190 to 240° C., $P_A$ is in a range of from 2000 to 15000 Pa, $T_B$ is in a range of from 190 to 240° C., and $P_B$ is in a range of from 2000 to 15000 Pa.

3. The process according to item 1 or 2, wherein each of said high boiling point material separating column A and said diphenyl carbonate purifying column B is a distillation column having a tray and/or a packing as said internal.

4. The process according to item 3, wherein said internal of each of said high boiling point material separating column A and said diphenyl carbonate purifying column B is a packing.

5. The process according to item 4, wherein said packing is a structured packing which is at least one selected from the group consisting of Mellapak, Gempak, TECHNO-PAK, FLEXI-PAK, a Sulzer packing, a Goodroll packing, and a Glitchgrid.

In the second aspect of the present invention, there is provided:

6. A high-purity diphenyl carbonate containing a halogen content of not more than 0.1 ppm, and a content of by-products having a higher boiling point than that of the diphenyl carbonate of not more than 100 ppm, produced by the process according to any one of claims 1 to 5.

7. The high-purity diphenyl carbonate according to item 6, wherein the halogen content is not more than 10 ppb, and the content of each of phenyl salicylate, xanthone, phenyl methoxybenzoate, and 1-phenoxycarbonyl-2-phenoxycarboxyphenylene, which are the by-products having the higher boiling point than that of the diphenyl carbonate, is not more than 30 ppm.

8. The high-purity diphenyl carbonate according to item 7, wherein the content of the by-products having the higher boiling point than that of the diphenyl carbonate is not more than 50 ppm.

9. The high-purity diphenyl carbonate according to item 8, wherein the halogen content is not more than 1 ppb, and the content of the by-products having the higher boiling point than that of the diphenyl carbonate is not more than 10 ppm.

In the third aspect of the present invention, there is provided:

10. An apparatus for producing a high-purity diphenyl carbonate which is produced from a reaction mixture containing a diphenyl carbonate, which has been obtained by carrying out a transestrification reaction between a dialkyl carbonate and a phenol and/or a disproportionation reaction of an alkyl carbonate and/or a transesterification reaction between an alkyl phenyl carbonate and a phenol in the presence of a homogeneous catalyst, the apparatus comprises;

a high boiling point material separating column A which receives said reaction mixture, and which carries out separation by distillation into a column top component $A_T$ containing the diphenyl carbonate and a column bottom component $A_B$ containing the catalyst; and a diphenyl carbonate purifying column B having a side cut outlet B2, which is connected with said high boiling point material separating column A, and which receives said column top component $A_T$ therefrom, wherein separation by distillation is carried out into a column top component $B_T$, a side cut component $B_S$ and a column bottom component $B_B$; wherein (a) said high boiling point material separating column A comprises a continuous multi-stage distillation column having a length $L_A$ (cm), an inside diameter $D_A$ (cm), and an internal with a number of stages $n_A$ thereinside, wherein $L_A$, $D_A$, and $n_A$ satisfy the following formulae (1) to (3);

$$800 \leq L_A \leq 3000 \qquad (1)$$

$$100 \leq D_A \leq 1000 \qquad (2)$$

$$20 \leq n_A \leq 100 \qquad (3);$$

(b) said diphenyl carbonate purifying column B comprises a continuous multi-stage distillation column having a length $L_B$ (cm), an inside diameter $D_B$ (cm), an internal thereinside, an inlet B1 at a middle portion of the column, and the side cut outlet B2 between said inlet B1 and the column bottom, in which a number of stages of the internal above the inlet B1 is $n_1$, a number of stages of the internal between the inlet B1 and the side cut outlet B2 is $n_2$, a number of stages of the internals below the side cut outlet B2 is $n_3$, and a total number of stages is $n_B$ ($=n_1+n_2+n_3$), wherein $L_B$, $D_B$, $n_1$, $n_2$, $n_3$, and $n_B$ satisfy the following formulae (4) to (9);

$$1000 \leq L_B \leq 5000 \qquad (4)$$

$$100 \leq D_B \leq 1000 \qquad (5)$$

$$5 \leq n_1 \leq 20 \qquad (6)$$

$$12 \leq n_2 \leq 40 \qquad (7)$$

$$3 \leq n_3 \leq 15 \qquad (8)$$

$$20 \leq n_B \leq 70 \qquad (9);$$

11. The apparatus according to item 10, wherein a distillation operation of said high boiling point material separating column A is carried out under conditions of a column bottom temperature $T_A$ in a range of from 185 to 280° C., and a column top pressure $P_A$ in a range of from 1000 to 20000 Pa.

12. The apparatus according to item 10 or 11, wherein a distillation operation of said diphenyl carbonate purifying column B is carried out under conditions of a column bottom temperature $T_B$ in a range of from 185 to 280° C., and a column top pressure $P_B$ in a range of from 1000 to 20000 Pa.

13. The apparatus according to any one of items 10 to 12, wherein not less than 1 ton/hr of the high-purity diphenyl carbonate is obtained as the side cut component $B_S$.

14. The apparatus according to any one of items 10 to 13, wherein $L_A$, $D_A$, and $n_A$ for said high boiling point material separating column A satisfy the following formulae: $1000 \leq L_A \leq 2500$, $200 \leq D_A \leq 600$, and $30 \leq n_A \leq 70$, respectively, $L_B$, $D_B$, $n_1$, $n_2$, $n_3$, and $n_B$ for said diphenyl carbonate purifying column B satisfy the following formulae: $1500 \leq L_B \leq 3000$, $150 \leq D_B \leq 500$, $7 \leq n_1 \leq 15$, $12 \leq n_2 \leq 30$, $3 \leq n_3 \leq 10$, and $25 \leq n_B \leq 55$, respectively, $T_A$ is in a range of from 190 to 240° C., $P_A$ is in a range of from 2000 to 15000 Pa, $T_B$ is in a range of from 190 to 240° C., and $P_B$ is in a range of from 2000 to 15000 Pa 15. The apparatus according to any one of items 10 to 14, wherein each of said high boiling point material separating column A and said diphenyl carbonate purifying column B is a distillation column having a tray and/or a packing as said internal.

16. The apparatus according to item 15, wherein said internal of each of said high boiling point material separating column A and said diphenyl carbonate purifying column B is a packing.

17. The apparatus according to item 16, wherein said packing is a structured packing which is at least one selected from the group consisting of Mellapak, Gempak, TECHNO-PAK, FLEXI-PAK, a Sulzer packing, a Goodroll packing, and a Glitchgrid.

In another aspect of the process according to the present invention, there is provided:

18. A process for the production of a high-purity diphenyl carbonate, the process comprising the steps of:

(i) carrying out a transestrification reaction between a dialkyl carbonate and a phenol and/or a disproportionation reaction of an alkyl carbonate and/or a transesterification reaction between an alkyl phenyl carbonate and a phenol in the presence of a homogeneous catalyst, so as to form a reaction mixture containing a diphenyl carbonate;

(ii) carrying out separation by distillation in a high boiling point material separating column A into a column top component $A_T$ containing the diphenyl carbonate and a column bottom component $A_B$ containing the catalyst (iii) carrying out separation by distillation of said column top component $A_T$ in a diphenyl carbonate purifying column B having a side cut outlet into a column top component $B_T$, a side cut component $B_S$ and a column bottom component $B_B$, said column top component $A_T$ introducing from the side cut outlet into the column B; wherein (a) said high boiling point material separating column A comprises a continuous multi-stage distillation column having a length $L_A$ (cm), an inside diameter $D_A$ (cm), and an internal with a number of stages $n_A$ thereinside, wherein $L_A$, $D_A$, and $n_A$ satisfy the following formulae (1) to (3);

$$800 \leq L_A \leq 3000 \qquad (1)$$

$$100 \leq D_A \leq 1000 \qquad (2)$$

$$20 \leq n_A \leq 100 \qquad (3);$$

(b) said diphenyl carbonate purifying column B comprises a continuous multi-stage distillation column having a length $L_B$ (cm), an inside diameter $D_B$ (cm), an internal thereinside, an inlet B1 at a middle portion of the column, and a side cut outlet B2 between said inlet B1 and the column bottom, in which a number of stages of the internal above the inlet B1 is $n_1$, a number of stages of the internal between the inlet B1 and the side cut outlet B2 is $n_2$, a number of stages of the internals below the side cut outlet B2 is $n_3$, and a total number of stages is $n_B$ (=$n_1+n_2+n_3$), wherein $L_B$, $D_B$, $n_1$, $n_2$, $n_3$, and $n_B$ satisfy the following formulae (4) to (9);

$$1000 \leq L_B \leq 5000 \qquad (4)$$

$$100 \leq D_B \leq 1000 \qquad (5)$$

$$5 \leq n_1 \leq 20 \qquad (6)$$

$$12 \leq n_2 \leq 40 \qquad (7)$$

$$3 \leq n_3 \leq 15 \qquad (8)$$

$$20 \leq n_B \leq 70 \qquad (9);$$

19. The process according to item 18, wherein not less than 1 ton/hr of the high-purity diphenyl carbonate is obtained as the side cut component $B_S$.

20. The process according to item 18 or 19, wherein $L_A$, $D_A$, and $n_A$ for said high boiling point material separating column A satisfy the following formulae: $1000 \leq L_A \leq 2500$, $200 \leq D_A \leq 600$, and $30 \leq n_A \leq 70$, respectively, $L_B$, $D_B$, $n_1$, $n_2$, $n_3$, and $n_B$ for said diphenyl carbonate purifying column B satisfy the following formulae: $1500 \leq L_B \leq 3000$, $150 \leq D_B \leq 500$, $7 \leq n_1 \leq 15$, $12 \leq n_2 \leq 30$, $3 \leq n_3 \leq 10$, and $25 \leq n_B \leq 55$, respectively, $T_A$ is in a range of from 190 to 240° C., $P_A$ is in a range of from 2000 to 15000 Pa, $T_B$ is in a range of from 190 to 240° C., and $P_B$ is in a range of from 2000 to 15000 Pa.

21. The process according to any one of items 18 to 20, wherein each of said high boiling point material separating column A and said diphenyl carbonate purifying column B is a distillation column having a tray and/or a packing as said internal.

22. The process according to item 21, wherein said internal of each of said high boiling point material separating column A and said diphenyl carbonate purifying column B is a packing.

23. The process according to item 22, wherein said packing is a structured packing which is at least one selected from the group consisting of Mellapak, Gempak, TECHNO-PAK, FLEXI-PAK, a Sulzer packing, a Goodroll packing, and a Glitchgrid.

ADVANTAGEOUS EFFECT OF THE INVENTION

It has been discovered that by implementing the present invention, a high-purity diphenyl carbonate that can be used as a raw material of a high-quality and high-performance polycarbonate can be produced on an industrial scale of not less than 1 ton/hr, preferably not less than 2 ton/hr, more preferably not less than 3 ton/hr, stably for a prolonged period of time of not less than 2000 hours, preferably not less than 3000 hours, more preferably not less than 5000 hours, from a reaction mixture containing the diphenyl carbonate that has been obtained by carrying out a transesterification reaction between a dialkyl carbonate and a phenol and/or a disproportionation reaction of an alkyl phenyl carbonate and/or a transesterification reaction between the alkyl phenyl carbonate and the phenol in the presence of a homogeneous catalyst.

BRIEF DESCRIPTION OF DRAWING

A1 and B1: inlet; B2: outlet; 11: outlet for a column bottom component of high boiling point material column A; 13 and 23: column top gas outlet; 14, 24, 18, 28, and 38: heat exchanger; 15 and 25; reflux liquid inlet; 16: outlet for a column top component of high boiling point material column A; 17 and 27; column bottom liquid outlet; 26: outlet for a column top component of diphenyl carbonate purifying column B; 31: outlet for a column bottom component of diphenyl carbonate purifying column B; 33: outlet for a side cut component of diphenyl carbonate purifying column B.

BEST MODE FOR CARRYING OUR THE INVENTION

In the following, the present invention is described in detail.

A dialkyl carbonate used in the present invention is a compound represented by the general formula (10);

$$R^1OCOOR^1 \qquad (10)$$

wherein $R^1$ represents an alkyl group having 1 to 10 carbon atoms, an alicyclic group having 3 to 10 carbon atoms, or an aralkyl group having 6 to 10 carbon atoms. Examples of $R^1$ include an alkyl group such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; an alicyclic group such as cyclopropyl, cyclobutyl, cyclopentyl, cyclohexyl and cycloheptyl; and an aralkyl group such as benzyl, phenethyl (isomers), phenylpropyl (isomers), phenylbutyl (isomers) and methylbenzyl (isomers). The above-mentioned alkyl groups, alicyclic group and aralkyl group may be substituted with other substituents such as la ower alkyl group, a lower alkoxy group, a cyano group or a halogen atom, and may also contain an unsaturated bond therein.

Examples of dialkyl carbonates having such $R^1$ include dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers).

Of these dialkyl carbonates, ones preferably used in the present invention are dialkyl carbonates in which $R^1$ is an alkyl group having not more than four carbon atoms and not containing a halogen atom. A particularly preferable one is dimethyl carbonate. Moreover, of preferable dialkyl carbonates, particularly preferable ones are dialkyl carbonates produced in a state substantially not containing a halogen, for example ones produced from an alkylene carbonate substantially not containing a halogen and an alcohol substantially not containing a halogen.

A phenol used in the present invention is one in which one hydroxyl group is bonded to a phenyl group, and may be phenol itself or a substituted phenol. Examples of the substituted phenols include various alkylphenols such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols such as methoxyphenol (isomers) and ethoxyphenol (isomers); and arylalkylphenols such as phenylpropylphenol (isomers). Of unsubstituted phenol and such substituted phenols, unsubstituted phenol is particularly preferable used in the present invention. Moreover, of these phenols, ones substantially not containing a halogen are preferably used in the present invention.

The molar ratio of the dialkyl carbonate to the phenol used in the starting material for use in the present invention must be in a range of from 0.1 to 10. Outside this range, the amount of unreacted starting material remaining relative to a prescribed amount of the desired diphenyl carbonate produced becomes high, which is not efficient, and moreover much energy is required to recover the unreacted starting material. For that reason, the above molar ratio is more preferably in a range of from 0.5 to 5, yet more preferably from 1 to 3.

A catalyst used in the present invention is a homogeneous catalyst which contains a metal such as Pb, Cu, Zn, Fe, Co, Ni, Al, Ti, V, Sn and the like, and which dissolves in the reaction system. A catalyst in which such a metallic component is bonded to organic groups can thus be preferably used. The catalyst component may of course have been reacted with an organic compound present in the reaction system such as aliphatic alcohols, phenols, alkyl phenyl carbonates, diphenyl carbonates or dialkyl carbonates, or may have been subjected to heating treatment with the starting material or products prior to the reaction. The catalyst used in the present invention is preferably one that has a high solubility in the reaction liquid under the reaction conditions. Examples of preferable catalysts in this sense include PbO, Pb(OH)$_2$ and Pb(OPh)$_2$; TiCl$_4$, Ti(OMe)$_4$, (MeO)Ti(OPh)$_3$, (MeO)$_2$Ti(OPh)$_2$, (MeO)$_3$Ti(OPh) and Ti(OPh)$_4$; SnCl$_4$, Sn(OPh)$_4$, Bu$_2$SnO and Bu$_2$Sn(OPh)$_2$; FeCl$_3$, Fe(OH)$_3$ and Fe(OPh)$_3$; and such catalysts that have been treated with phenol, the reaction liquid and the like.

In the present invention, it is particularly preferable to use a starting material and catalyst not containing a halogen. In this case, the diphenyl carbonate produced does not contain a halogen at all, and hence it is important as a raw material when industrially producing a polycarbonate by means of a transesterification method. The reason is that even if a halogen is present in the raw material for the polymerization in even an amount less than, for example, 1 ppm, then this halogen does inhibit the polymerization reaction, and cause a deterioration in the properties of the polycarbonate produced, and cause discoloration of the polycarbonate.

The process for the production of the reaction mixture containing the diphenyl carbonate using such a homogeneous catalyst with the dialkyl carbonate and the phenol as a starting material may be any process, but one particularly preferable for industrial implementation is a process in which two continuous multi-stage distillation columns are used as reactive distillation columns as previously proposed by the present inventors. This is a process in which a transesterification reaction between the dialkyl carbonate and the phenol is carried out in the presence of the homogeneous catalyst in the first continuous multi-stage distillation column to obtain a column bottom reaction mixture having an alkyl phenyl carbonate as a main product therein, and this column bottom reaction mixture is introduced into the second continuous multi-stage distillation column, where conversion of the alkyl phenyl carbonate into the diphenyl carbonate and the dialkyl carbonate occurs mainly through a disproportionation reaction. The diphenyl carbonate may of course also be produced through a transesterification reaction between the alkyl phenyl carbonate and the phenol in the reactive distillation columns. The column bottom reaction mixture from the second continuous multi-stage distillation column thus obtained is preferably taken as the reaction mixture containing the diphenyl carbonate used in the present invention.

Note that since the disproportionation reaction is a transesterification reaction between two of the same molecular species, the "reaction mixture containing the diphenyl carbonate, which has been obtained by carrying out a transesterification reaction between a dialkyl carbonate and a phenol and/or a disproportionation reaction of an alkyl phenyl carbonate and/or a transesterification reaction between the alkyl phenyl carbonate and the phenol in the presence of a homogeneous catalyst" used in the present invention can also be referred to as a "reaction mixture containing the diphenyl carbonate, which has been obtained through transesterification reaction between a dialkyl carbonate and a phenol as a starting material in the presence of a homogeneous catalyst". When "reaction mixture" is used merely in the present invention, such a reaction mixture is meant.

In addition to the diphenyl carbonate, the reaction mixture used in the present invention contains the catalyst, unreacted starting materials, the alkyl phenyl carbonate, by-products and so on. As the by-products, there are relatively low boiling point by-products such as an alkyl phenyl ether, and the high boiling point by-products such as Fries rearrangement products of the alkyl phenyl carbonate or the diphenyl carbonate and derivatives thereof, degeneration products of the diphenyl carbonate, and other high boiling point material of an unknown structure.

For example, in the case of producing diphenyl carbonate using dimethyl carbonate and phenol as a starting material, reaction by-products are anisole, methyl salicylate, phenyl salicylate, xanthone, phenyl methoxybenzoate, 1-phenoxycarbonyl-2-phenoxycarboxy-phenylene and so on, and typically a small amount of high boiling point by-products of unknown structure thought to be produced through further reaction of these reaction by-products is also contained.

In one embodiment of the present invention, such a reaction mixture is continuously introduced into a high boiling point material separating column A, and continuously separated into a column top component $A_T$ containing the diphenyl carbonate and a column bottom component $A_B$ containing the catalyst, and then the column top component $A_T$ is continuously introduced into a diphenyl carbonate purifying column B having a side cut outlet, and continuously separated by distillation into a column top component $B_T$, a side cut component $B_S$ and a column bottom component $B_B$. In this way, not less than 1 ton/hr of a high-purity diphenyl carbonate is obtained continuously as the side cut component $B_S$. For this purpose, the high boiling point material separating column A and the diphenyl carbonate purifying column B must each be made to be a continuous multi-stage distillation column having a specified structure, and must be used in combination with one another.

The reaction mixture used in the present invention generally contains 50 to 80% by weight of the diphenyl carbonate based on 100% by weight of the reaction mixture, and hence to obtain not less than 1 ton/hr of the high-purity diphenyl carbonate, the amount of the reaction mixture continuously introduced into the high boiling point material separating column A is not less than approximately 1.3 to 2 ton/hr, although this amount varies depending on the content of the diphenyl carbonate. It is generally necessary to subject more than 2 ton/hr of the reaction mixture to the separation/purification.

Figure 1:
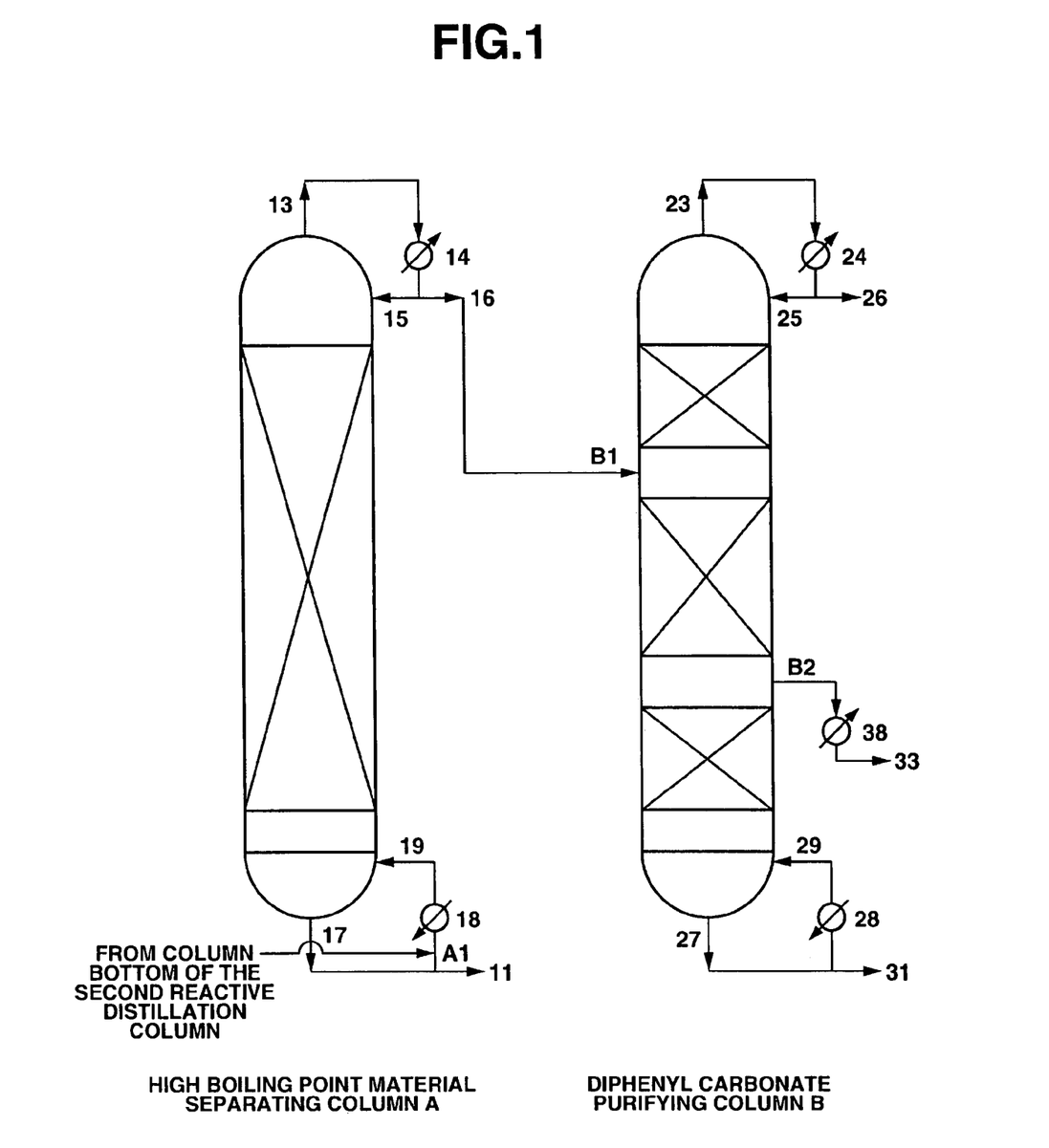
FIG. 1 is a schematic view of an example showing a continuous separating/purifying apparatus for carrying out the present invention in which a high boiling point material separating column A and a diphenyl carbonate purifying column B are connected together. As one example, each of these continuous multi-stage distillation columns has installed therein an internal comprising a structured packing having a predetermined number of stages.

FIG. 1 illustrates a schematic view of an example showing a continuous separating/purifying apparatus for carrying out the present invention in which a high boiling point material separating column A and a diphenyl carbonate purifying column B are connected together. As one example, each of the high boiling point material separating column A and the diphenyl carbonate purifying column comprises a continuous multi-stage distillation columns having therein an internal comprising, but is not limited to, a structured packing having a predetermined number of stages. Note that the columns A and B comprise the following structures, respectively, in order to carry out the producing process according to the present invention.

In the producing process according to the present invention, the high boiling point material separating column A must be a continuous multi-stage distillation column having a length $L_A$ (cm), an inside diameter $D_A$ (cm), and an internal with a number of stages $n_A$ thereinside, wherein $L_A$, $D_A$, and $n_A$ satisfy the following formulae (1) to (3):

$$800 \leq L_A \leq 3000 \quad (1)$$

$$100 \leq D_A \leq 1000 \quad (2)$$

$$20 \leq n_A \leq 100 \quad (3).$$

Moreover, the distillation conditions for the high boiling point material separating column A must be a column bottom temperature $T_A$ in a range of from 185 to 280° C., and a column top pressure $P_A$ in a range of from 1000 to 20000 Pa.

Furthermore, the diphenyl carbonate purifying column B must be a continuous multi-stage distillation column having a length $L_B$ (cm), an inside diameter $D_B$ (cm), an internal thereinside, an inlet B1 at a middle portion of the column, and a side cut outlet B2 between said inlet B1 and the column bottom, in which a number of stages of the internal above the inlet B1 is $n_1$, a number of stages of the internal between the inlet B1 and the side cut outlet B2 is $n_2$, a number of stages of the internals below the side cut outlet B2 is $n_3$, and a total number of stages is $n_B$ ($=n_1+n_2+n_3$), wherein $L_B$, $D_B$, $n_1$, $n_2$, $n_3$, and $n_B$ satisfy the following formulae (4) to (9):

$$1000 \leq L_B \leq 5000 \quad (4)$$

$$100 \leq D_B \leq 1000 \quad (5)$$

$$5 \leq n_1 \leq 20 \quad (6)$$

$$12 \leq n_2 \leq 40 \quad (7)$$

$$3 \leq n_3 \leq 15 \quad (8)$$

$$20 \leq n_B \leq 70 \quad (9);$$

Moreover, the distillation conditions for the diphenyl carbonate purifying column B must be a column bottom temperature $T_B$ in a range of from 185 to 280° C., and a column top pressure $P_B$ in a range of from 1000 to 20000 Pa.

It has been discovered that by using the high boiling point material separating column A and the diphenyl carbonate purifying column B simultaneously satisfying all of these conditions, a high-purity diphenyl carbonate can be purified and produced on an industrial scale of not less than 1 ton/hr stably for a prolonged period of time, for example not less than 2000 hours, preferably not less than 3000 hours, more preferably not less than 5000 hours, from a reaction mixture containing the diphenyl carbonate that has been obtained through transesterification reaction between a dialkyl carbonate and a phenol as a starting material in the presence of a homogeneous catalyst. The reason why it has become possible to produce the high-purity diphenyl carbonate on an industrial scale with such excellent effects by implementing the process of the present invention is not clear, but this is supposed to be due to a combined effect between the distillation conditions and an effect brought about when the conditions of formulae (1) to (9) are combined. Preferable ranges for the respective factors are described below.

If $L_A$ (cm) is less than 800, since a height of the internal which can be installed in the high boiling point material separating column A becomes limited, the separation efficiency decreases, and it is thus undesirable for $L_A$ (cm). Moreover, to keep down the equipment cost while attaining the desired separation efficiency, $L_A$ must be made to be not more than 3000. A more preferable range for $L_A$ (cm) is $1000 \leq L_A \leq 2500$, with $1200 \leq L_A \leq 2000$ being yet more preferable.

If $D_A$ (cm) is less than 100, then it is not possible to attain the desired production amount. Moreover, to keep down the equipment cost while attaining the desired production amount, $D_A$ must be made to be not more than 1000. A more preferable range for $D_A$ (cm) is $200 \leq D_A \leq 600$, with $250 \leq D_A \leq 450$ being yet more preferable.

If $n_A$ is less than 20, then the separation efficiency decreases, and hence the desired high purity cannot be attained. Moreover, to keep down the equipment cost while attaining the desired separation efficiency, $n_A$ must be made to be not more than 100. Furthermore, if $n_A$ is greater than 100, then the pressure difference between the top and bottom of the column becomes too great, and hence prolonged stable operation of the high boiling point material separating column A becomes difficult. Moreover, it becomes necessary to increase the temperature in the lower portion of the column, and hence side reactions become liable to occur, which is undesirable. A more preferable range for $n_A$ is $30 \leq n_A \leq 70$, with $35 \leq n_A \leq 60$ being yet more preferable.

If $T_A$ is less than 185° C., since the column top pressure must be reduced, equipment for maintaining a high vacuum must be used, and moreover the equipment increases in size. Moreover, it is undesirable for $T_A$ to be greater than 280° C., because the high boiling point by-products are produced during the distillation. A more preferable range for $T_A$ is from 190 to 240° C., with from 195 to 230° C. being yet more preferable.

It is undesirable for $P_A$ to be less than 1000 Pa, since then large equipment enabling a high vacuum to be maintained must be used. Moreover, it is undesirable for $P_A$ to be greater than 20000 Pa, since then the distillation temperature must be increased and hence production of by-products increases. A more preferable range for $P_A$ is from 2000 to 15000 Pa, with from 3000 to 13000 Pa being yet more preferable.

If $L_B$ (cm) is less than 1000, since a height of the internal which can be installed in the diphenyl carbonate purifying column B becomes limited, the separation efficiency decreases, and it is thus undesirable for $L_B$ (cm). Moreover, to keep down the equipment cost while attaining the desired separation efficiency, $L_B$ must be made to be not more than 5000. A more preferable range for $L_B$ (cm) is $1500 \leq L_B \leq 3000$, with $1700 \leq L_B \leq 2500$ being yet more preferable.

If $D_B$ (cm) is less than 100, then it is not possible to attain the desired production amount. Moreover, to keep down the equipment cost while attaining the desired production amount, $D_B$ must be made to be not more than 1000. A more preferable range for $D_B$ (cm) is $150 \leq D_B \leq 500$, with $200 \leq D_B \leq 400$ being yet more preferable.

If $n_B$ is less than 20, then the separation efficiency for the column as a whole decreases, and hence the desired high purity cannot be attained. Moreover, to keep down the equipment cost while attaining the desired separation efficiency, $n_B$ must be made to be not more than 70. Furthermore, if $n_B$ is greater than 70, then the pressure difference between the top and bottom of the column becomes too great, and hence prolonged stable operation of the diphenyl carbonate purifying column B becomes difficult. Moreover, it becomes necessary to increase the temperature in the lower portion of the column, and hence side reactions become liable to occur, which is undesirable. A more preferable range for $n_B$ is $25 \leq n_B \leq 55$, with $30 \leq n_B \leq 50$ being yet more preferable. Furthermore, it has been ascertained that to obtain the desired high-purity diphenyl carbonate stably for a prolonged period of time, $n_1$, $n_2$, and $n_3$ must be in the ranges $5 \leq n_1 \leq 20$, $12 \leq n_2 \leq 40$, and $3 \leq n_3 \leq 15$, respectively. More preferable ranges are $7 \leq n_1 \leq 15$, $12 \leq n_2 \leq 30$, and $3 \leq n_3 \leq 10$.

It is undesirable for $T_B$ to be less than 185° C., since then the column top pressure must be reduced, and hence equipment for maintaining a high vacuum must be used, and moreover the equipment increases in size. Moreover, it is undesirable for $T_B$ to be greater than 280° C., since then high boiling point by-products are produced during the distillation. A more preferable range for $T_B$ is from 190 to 240° C., with from 195 to 230° C. being yet more preferable.

It is undesirable for $P_B$ to be less than 1000 Pa, since then large equipment enabling a high vacuum to be maintained must be used. Moreover, it is undesirable for $P_B$ to be greater than 20000 Pa, since then the distillation temperature must be increased and hence production of by-products increases. A more preferable range for $P_B$ is from 2000 to 15000 Pa, with from 3000 to 13000 Pa being yet more preferable.

For the high boiling point material separating column A and the diphenyl carbonate purifying column B, so long as $D_A$ and $D_B$ are within the above ranges, each of the columns may have the same inside diameter from the upper portion thereof to the lower portion thereof, or the inside diameter may differ in different portions. For example, for each of the continuous multi-stage distillation columns, the inside diameter of the upper portion of the column may be smaller than, or larger than, the inside diameter of the lower portion of the column.

Each of the high boiling point material separating column A and the diphenyl carbonate purifying column B used in the present invention is a distillation column having a tray and/or a packing as the internal. The term "internal" used in the present invention means the parts in the distillation column where gas and liquid are actually brought into contact with one another. As the tray, for example, a bubble-cap tray, a sieve tray, a valve tray, a counterflow tray, a Superfrac tray, a Maxfrac tray or the like are preferable. As the packing, irregular packings such as a Raschig ring, a Lessing ring, a Pall ring, a Berl saddle, an Intalox saddle, a Dixon packing, a McMahon packing or Heli-Pak, or a structured packing such as Mellapak, Gempak, TECHNO-PAK, Flexipac, a Sulzer packing, a Goodroll packing or a Glitchgrid are preferable. The multi-stage distillation column having both a tray portion and a portion packed with the packing can also be used. Note that the term "number of stages (n) of an internal" used in the present invention means that the total number of trays in the case of a tray, and the theoretical number of stages in the case of the packing. Accordingly, in the case of the multi-stage column having both the tray portion and the portion packed with the packing, n means the sum of the total number of trays and the theoretical number of stages of the packing.

It has been ascertained that the high boiling point material separating column A according to the present invention preferably comprises the packing as the internal, and furthermore a structured packing is preferable as the packing. It has also been discovered that the diphenyl carbonate purifying column B according to the present invention preferably comprises the packing as the internal, particularly preferably one or more of the structured packing.

A process in which transesterification reaction is carried out with a dialkyl carbonate and a phenol as a starting material in the presence of a homogeneous catalyst using an apparatus in which two reactive distillation columns are connected together is a preferable process for obtaining the reaction mixture that acts as the starting material in the present invention. In this case, a column bottom liquid continuously withdrawn from the bottom of the second reactive distillation column can be used as the reaction mixture used in the present invention. This reaction mixture continuously withdrawn from the bottom of the second reactive distillation column generally contains 0.05 to 2% by weight of the dialkyl carbonate, 1 to 20% by weight of the phenol, 0.05 to 2% by weight of an alkyl phenyl ether, 10 to 45% by weight of an alkyl phenyl carbonate, 50 to 80% by weight of the diphenyl carbonate, 0.1 to 5% by weight of high boiling point by-products, and 0.001 to 5% by weight of the catalyst, based on the 100% by weight of the reaction mixture.

The composition of the reaction mixture varies depending on the conditions of the transesterification reaction between the dialkyl carbonate and the phenol, the type and amount of the catalyst and so on, but so long as the transesterification reaction is carried out under constant conditions, a reaction mixture of approximately constant composition can be produced, and hence the composition of the reaction mixture fed into the high boiling point material separating column A may be approximately constant. However, in the present invention, so long as the composition of the reaction mixture is within the above range, then even if this composition fluctuates somewhat, the separation can still be carried out with approximately the same separation efficiency. This is one of the characteristic features of the present invention.

In the present invention, when continuously feeding the reaction mixture that acts as the starting material into the high boiling point material separating column A, the reaction mixture may be fed in a liquid from into inlet(s) provided in one or a plurality of positions below a middle portion of the separating column A, or it is also preferable to feed the reaction mixture into the column via a reboiler of the separating column A from piping provided at a lower portion of the reboiler. The amount of the reaction mixture fed into the high boiling point material separating column A varies depending on the amount of the high-purity diphenyl carbonate to be produced, the concentration of the diphenyl carbonate in the reaction mixture, the separation conditions for the separating column A and so on, but the above amount is generally not less than 2 ton/hr, preferably not less than 6 ton/hr, more preferably not less than 10 ton/hr. The upper limit of the amount of the reaction mixture fed into varies depending on the size of the apparatus, the required production amount and so on, but the upper limit is generally 200 ton/hr. The reaction mixture fed continuously into the high boiling point material separating column A is separated into a column top component ($A_T$) containing most of the diphenyl carbonate and most of compounds having a lower boiling point than that of the diphenyl carbonate, such as unreacted starting material, an alkyl phenyl ether and an alkyl phenyl carbonate, and a column bottom component ($A_B$) containing the catalyst, high boiling point by-products and a small amount of the diphenyl carbonate.

The column bottom component ($A_B$) may contain a small amount of the alkyl phenyl carbonate. Such organic material in the column bottom component ($A_B$) plays a useful role in dissolving the catalyst component and thus maintaining a liquid state of the column bottom component ($A_B$). All or some of the column bottom component ($A_B$) is generally reused by recycling to the first reactive distillation column as a transesterification reaction catalyst component, but in some cases the catalyst may be recycled after being separated from the organic material in a catalyst recovery process, and then reused by recycling to the first reactive distillation column.

It is a characteristic feature of the present invention that the catalyst component and by-products having a higher boiling point than that of the diphenyl carbonate such as phenyl salicylate, xanthone, phenyl methoxybenzoate and 1-phenoxycarbonyl-2-phenoxycarboxy-phenylene are almost completely removed as the column bottom component ($A_B$) in the high boiling point material separating column A, it being easy to make the content thereof in the column top component ($A_T$) be generally not more than 200 ppm, preferably not more than 100 ppm, more preferably not more than 50 ppm. It is another characteristic feature of the present invention that despite making the column top component ($A_T$) hardly contain any such high boiling point by-products, most of the diphenyl carbonate in the reaction mixture introduced can be withdrawn from the top of the column. In the present invention, not less than 95%, preferably not less than 96%, more preferably not less than 98%, of the diphenyl carbonate in the reaction mixture continuously fed into the high boiling point material separating column A can be withdrawn from the top of the column. Moreover, in the present invention, although dependent on the composition of the reaction mixture fed into the separating column A, typically 90 to 97% by weight of the liquid continuously fed in is continuously withdrawn from the top of the column as the column top component ($A_T$), with 10 to 3% being continuously withdrawn from the bottom of the column as the column bottom component ($A_B$). The composition of the column top component ($A_T$) is generally 0.05 to 2% by weight of the dialkyl carbonate, 1 to 21% by weight of the phenol, 0.05 to 2% by weight of an alkyl phenyl ether, 11 to 47% by weight of the alkyl phenyl carbonate, and 52 to 84% by weight of the diphenyl carbonate, based on 100% by weight of the column top component ($A_T$). The content of the high boiling point by-products is generally not more than 200 ppm, preferably not more than 100 ppm, more preferably not more than 50 ppm.

In the present invention, the reflux ratio for the high boiling point material separating column A is in a range of from 0.01 to 10, preferably from 0.08 to 5, more preferably from 0.1 to 3.

As stated above, the amount of the column top component ($A_T$) continuously withdrawn from the top of the high boiling point material separating column A is generally approximately 90 to 97% of the reaction mixture fed into the separating column A. This column top component ($A_T$) is continuously fed into the diphenyl carbonate purifying column B from the inlet B1 provided at an intermediate portion of the purifying column B, and is continuously separated into three components, i.e. a column top component ($B_T$), a side cut component ($B_S$), and a column bottom component ($B_B$). All of components having a lower boiling point than that of the diphenyl carbonate contained in the column top component ($A_T$) from the separating column A fed into the purifying column B are continuously withdrawn from the top of the purifying column B as the column top component ($B_T$), and a small amount of liquid is continuously withdrawn from the bottom of the purifying column B. A small amount of the diphenyl carbonate is contained in the column top component ($B_T$), this amount generally being 1 to 9%, preferably 3 to 8%, of the diphenyl carbonate fed in. The diphenyl carbonate in the column top component ($B_T$) is separated out and thus recovered in another distillation column used for separating the column top component ($B_T$). Alternatively, a method in which this diphenyl carbonate is separated off as the column bottom component from this other distillation column, and is then recovered by being returned into the high boiling point material separating column A and/or the diphenyl carbonate purifying column B is also preferable.

The column bottom component ($B_B$) contains the diphenyl carbonate, and a small amount of high boiling point by-products concentrated to approximately a few percent. Another characteristic feature of the present invention is that the amount of the diphenyl carbonate in the column bottom component ($B_B$) withdrawn from the bottom of the purifying column B can be kept very low. This amount is generally 0.05 to 0.5% of the diphenyl carbonate fed in.

The high-purity diphenyl carbonate is continuously withdrawn from the side cut outlet B2 at a flow rate of generally not less than 1 ton/hr, preferably not less than 3 ton/hr, more preferably not less than 5 ton/hr. This amount generally corresponds to approximately 90 to 96% of the diphenyl carbonate fed into the purifying column B.

The purity of the diphenyl carbonate obtained as the side cut component ($B_S$) in the present invention is generally not less than 99.9%, preferably not less than 99.99%, more preferably not less than 99.999%. The contents of high boiling point impurities when carrying out the present invention with dimethyl carbonate and phenol as the starting material are not more than 30 ppm, preferably not more than 10 ppm, more preferably not more than 1 ppm for phenyl salicylate, not more than 30 ppm, preferably not more than 10 ppm, more preferably not more than 1 ppm for xanthone, not more than 30 ppm, preferably not more than 10 ppm, more preferably not more than 1 ppm for phenyl methoxybenzoate, and not more than 30 ppm, preferably not more than 10 ppm, more preferably not more than 5 ppm for 1-phenoxycarbonyl-2-phenoxycarboxy-phenylene. Moreover, the total content of these high boiling point by-products is not more than 100 ppm, preferably not more than 50 ppm, more preferably not more than 10 ppm. Note that the term "high-purity diphenyl carbonate" used in the present invention means that the purity of the diphenyl carbonate is not less than 99.9 and the diphenyl carbonate contains not more than 100 ppm of high boiling point by-products.

Moreover, in the present invention, a starting material and catalyst not containing a halogen are generally used, and hence the halogen content of the diphenyl carbonate obtained is not more than 0.1 ppm, preferably not more than 10 ppb, more preferably not more than 1 ppb.

In the present invention, the reflux ratio for the diphenyl carbonate purifying column B is in a range of from 0.01 to 10, preferably from 0.1 to 8, more preferably from 0.5 to 5.

The material constituting the high boiling point material separating column A, the diphenyl carbonate purifying column B, and other liquid-contacting parts which are used in the present invention is generally a metallic material such as carbon steel or stainless steel. In terms of the quality of the diphenyl carbonate produced, stainless steel is preferable.

EXAMPLES

Hereinbelow, the present invention will be described in more detail with reference to the following Examples, but the present invention is not limited to the following Examples.

The purity of the diphenyl carbonate, and the contents of impurities were measured by means of a gas chromatography method, and the halogen content was measured by means of an ion chromatography method.

Example 1

High Boiling Point Material Separating Column A

A continuous multi-stage distillation column as shown in FIG. 1 having $L_A=1700$ cm and $D_A=340$ cm, and having Mellapak with $n_A=30$ installed therein as the internal was used as the separating column A.

<Diphenyl Carbonate Purifying Column B>

A continuous multi-stage distillation column as shown in FIG. 1 having $L_B=2200$ cm and $D_B=280$ cm, and having three sets of Mellapak with $n_1=12$, $n_2=18$, and $n_3=5$ installed therein as the internal was used as the purifying column B.

<Reactive Distillation>

An apparatus in which two reactive distillation columns (a first reactive distillation column and a second reactive distillation column) were connected together was used, the reaction liquid in the first reactive distillation column was made to contain 100 ppm of $Pb(OPh)_2$ as a catalyst, reactive distillation was carried out using dimethyl carbonate and phenol as a starting material, and a reaction mixture containing diphenyl carbonate was continuously withdrawn at 13.1 ton/hr from the column bottom of the second reactive distillation column. Note that halogens were not detected in the starting material or the catalyst used in the reaction.

The composition of the reaction mixture was 0.1% by weight of dimethyl carbonate, 0.1% by weight of anisole, 6.3% by weight of phenol, 32.2% by weight of methyl phenyl carbonate, 58.6% by weight of diphenyl carbonate, and 2.7% by weight of high boiling point by-products including the catalyst.

<Separation/Purification>

Using an apparatus comprising the high boiling point material separating column A and the diphenyl carbonate purifying column B as shown in FIG. 1, the reaction mixture obtained through the reactive distillation described above was continuously introduced at 13.1 ton/hr into the separating column A from the inlet A1. The column bottom temperature ($T_A$) was made to be 206° C. and the column top pressure ($P_A$) was made to be 3800 Pa in the separating column A, distillation was carried out continuously with a reflux ratio of 0.6, a column top component ($A_T$) was continuously withdrawn at 12.5 ton/hr via a conduit 16, and a column bottom component ($A_B$) was continuously withdrawn at 0.6 ton/hr via a conduit 11. The column top component ($A_T$) was continuously introduced as is into the purifying column B from the inlet B1. The column bottom temperature ($T_B$) was made to be 213° C. and the column top pressure ($P_B$) was made to be 5000 Pa in the purifying column B, distillation was carried out continuously with a reflux ratio of 1.5, a column top component ($B_T$) was continuously withdrawn at 5.3 ton/hr via a conduit 26, a column bottom component ($B_B$) was continuously withdrawn at 0.03 ton/hr via a conduit 31, and a side cut component ($B_S$) was continuously withdrawn at 7.17 ton/hr via a conduit 33.

The compositions of the components at 24 hours after the system had become completely stable were as follows.

$A_T$: 0.1% by weight of dimethyl carbonate, 0.1% by weight of anisole, 6.6% by weight of phenol, 33.8% by weight of methyl phenyl carbonate, 59.4% by weight of diphenyl carbonate;

$A_B$: 41.0% by weight of diphenyl carbonate, 59.0% by weight of high boiling point material including a catalyst component and by-products having a higher boiling point than that of diphenyl carbonate such as phenyl salicylate, xanthone, phenyl methoxybenzoate and 1-phenoxycarbonyl-2-phenoxycarboxy-phenylene;

$B_T$: 0.25% by weight of dimethyl carbonate, 0.25% by weight of anisole, 15.6% by weight of phenol, 79.6% by weight of methyl phenyl carbonate, 4.3% by weight of diphenyl carbonate;

$B_B$: 95.0% by weight of diphenyl carbonate, 5.0% by weight of the high boiling point material.

The content of each of phenyl salicylate, xanthone and phenyl methoxybenzoate in the side cut component was not more than 1 ppm, and the content of 1-phenoxycarbonyl-2-phenoxycarboxy-phenylene was 4 ppm. Moreover, the halogen content was not more than 1 ppb. It was thus found that the purity of the diphenyl carbonate obtained from the side cut was not less than 99.999%. Moreover, the amount of this high-purity diphenyl carbonate produced was 7.17 ton/hr.

Prolonged continuous operation was carried out under these conditions. The amount of diphenyl carbonate produced and the purity were substantially unchanged after 500 hours, 2000 hours, 4000 hours, 5000 hours, and 6000 hours.

Example 2

Reactive Distillation

An apparatus in which two reactive distillation columns (a first reactive distillation column and a second reactive distillation column) were connected together was used, the reaction liquid in the first reactive distillation column was made to contain 250 ppm of $Pb(OPh)_2$ as a catalyst, reactive distillation was carried out using dimethyl carbonate and phenol as a starting material, and a reaction mixture containing diphenyl carbonate was continuously withdrawn at 11.3 ton/hr from the column bottom of the second reactive distillation column. Note that halogens were not detected in the starting material or the catalyst used in the reaction.

The composition of the reaction mixture was 0.1% by weight of dimethyl carbonate, 0.1% by weight of anisole, 2.5% by weight of phenol, 33.2% by weight of methyl phenyl carbonate, 62.5% by weight of diphenyl carbonate, and 1.6% by weight of high boiling point by-products including the catalyst.

<Separation/Purification>

Using an apparatus comprising the high boiling point material separating column A and the diphenyl carbonate purifying column B as shown in Example 1, the reaction mixture obtained through the reactive distillation described above was continuously introduced at 11.3 ton/hr into the separating column A from the inlet A1. The column bottom temperature ($T_A$) was made to be 205° C. and the column top pressure ($P_A$) was made to be 4000 Pa in the separating column A, distillation was carried out continuously with a reflux ratio of 0.7, a column top component ($A_T$) was continuously withdrawn at 11.0 ton/hr via the conduit 16, and a column bottom component ($A_B$) was continuously withdrawn at 0.3 ton/hr via the conduit 11. The column top component ($A_T$) was continuously introduced as is into the purifying column B from the inlet B1. The column bottom temperature ($T_B$) was made to be 210° C. and the column top pressure ($P_B$) was made to be 4500 Pa in the purifying column B, distillation was carried out continuously with a reflux ratio of 2.0, a column top component ($B_T$) was continuously withdrawn at 4.7 ton/hr via the conduit 26, a column bottom component ($B_B$) was continuously withdrawn at 0.03 ton/hr via the conduit 31, and a side cut component ($B_S$) was continuously withdrawn at 6.27 ton/hr via the conduit 33.

The compositions of the components at 24 hours after the system had become completely stable were as follows.

$A_T$: 0.1% by weight of dimethyl carbonate, 0.1% by weight of anisole, 2.6% by weight of phenol, 34.1% by weight of methyl phenyl carbonate, 63.1% by weight of diphenyl carbonate;

$A_B$: 40.2% by weight of diphenyl carbonate, 59.8% by weight of the high boiling point material including a catalyst component and by-products having a higher boiling point than that of diphenyl carbonate such as phenyl salicylate, xanthone, phenyl methoxybenzoate and 1-phenoxycarbonyl-2-phenoxycarboxy-phenylene;

$B_T$: 0.3% by weight of dimethyl carbonate, 0.2% by weight of anisole, 6.1% by weight of phenol, 79.8% by weight of methyl phenyl carbonate, 13.6% by weight of diphenyl carbonate;

$B_B$: 96.0% by weight of diphenyl carbonate, 4.0% by weight of the high boiling point material.

The content of each of phenyl salicylate, xanthone and phenyl methoxybenzoate in the side cut component was not more than 1 ppm, and the content of 1-phenoxycarbonyl-2-phenoxycarboxy-phenylene was 3 ppm. Moreover, the halogen content was not more than 1 ppb. It was thus found that the purity of the diphenyl carbonate obtained from the side cut was not less than 99.999%. Moreover, the amount of this high-purity diphenyl carbonate produced was 6.27 ton/hr.

Prolonged continuous operation was carried out under these conditions. The amount of diphenyl carbonate produced and the purity were substantially unchanged after 500 hours, 1000 hours, and 2000 hours.

Example 3

Reactive Distillation

An apparatus in which two reactive distillation columns (a first reactive distillation column and a second reactive distillation column) were connected together was used, the reaction liquid in the first reactive distillation column was made to contain 150 ppm of $Pb(OPh)_2$ as a catalyst, reactive distillation was carried out using dimethyl carbonate and phenol as a starting material, and a reaction mixture containing diphenyl carbonate was continuously withdrawn at 17.2 ton/hr from the bottom of the second reactive distillation column. Note that halogens were not detected in the starting material or the catalyst used in the reaction.

The composition of the reaction mixture was 0.2% by weight of dimethyl carbonate, 0.1% by weight of anisole, 6.6% by weight of phenol, 30.2% by weight of methyl phenyl carbonate, 60.1% by weight of diphenyl carbonate, and 2.8% by weight of high boiling point by-products including the catalyst.

<Separation/Purification>

Using an apparatus comprising a high boiling point material separating column A and a diphenyl carbonate purifying column B as shown in Example 1, the reaction mixture obtained through the reactive distillation described above was continuously introduced at 17.2 ton/hr into the separating column A from the inlet A1. The column bottom temperature ($T_A$) was made to be 207° C. and the column top pressure ($P_A$) was made to be 4100 Pa in the separating column A, distillation was carried out continuously with a reflux ratio of 0.61, a column top component ($A_T$) was continuously withdrawn at 16.4 ton/hr via the conduit 16, and a column bottom component ($A_B$) was continuously withdrawn at 0.8 ton/hr via the conduit 11. The column top component ($A_T$) was continuously introduced as is into the purifying column B from the inlet B1. The column bottom temperature ($T_B$) was made to be 220° C. and the column top pressure ($P_B$) was made to be 6600 Pa in the purifying column B, distillation was carried out continuously with a reflux ratio of 1.49, a column top component ($B_T$) was continuously withdrawn at 7.1 ton/hr via the conduit 26, a column bottom component ($B_B$) was continuously withdrawn at 0.05 ton/hr via the conduit 31, and a side cut component ($B_S$) was continuously withdrawn at 9.25 ton/hr via the conduit 33.

The compositions of the components at 24 hours after the system had become completely stable were as follows.

$A_T$: 0.2% by weight of dimethyl carbonate, 0.1% by weight of anisole, 6.9% by weight of phenol, 31.7% by weight of methyl phenyl carbonate, 61.1% by weight of diphenyl carbonate;

$A_B$: 39.8% by weight of diphenyl carbonate, 61.2% by weight of high boiling point material including a catalyst component and by-products having a higher boiling point than that of diphenyl carbonate such as phenyl salicylate, xanthone, phenyl methoxybenzoate and 1-phenoxycarbonyl-2-phenoxycarboxy-phenylene;

$B_T$: 0.5% by weight of dimethyl carbonate, 0.2% by weight of anisole, 16.0% by weight of phenol, 73.2% by weight of methyl phenyl carbonate, 10.1% by weight of diphenyl carbonate;

$B_B$: 94.0% by weight of diphenyl carbonate, 6.0% by weight of high boiling point material.

The content of each of phenyl salicylate, xanthone and phenyl methoxybenzoate in the side cut component was not more than 1 ppm, and the content of 1-phenoxycarbonyl-2-phenoxycarboxy-phenylene was 4 ppm. Moreover, the halogen content was not more than 1 ppb. It was thus found that the purity of the diphenyl carbonate obtained from the side cut was not less than 99.999%. Moreover, the amount produced of this high-purity diphenyl carbonate was 9.25 ton/hr.

Prolonged continuous operation was carried out under these conditions. The amount of diphenyl carbonate produced and the purity were substantially unchanged after 500 hours, 1000 hours, and 2000 hours.

INDUSTRIAL APPLICABILITY

The present invention can be suitably used in the field of producing a high-purity diphenyl carbonate, which can be used as a raw material of a high-quality and high-performance polycarbonate, stably for a prolonged period of time on an industrial scale of not less than 1 ton/hr from a reaction mixture containing a catalyst and reaction by-products that has been obtained through transesterification reaction or the like using a dialkyl carbonate and a phenol as a starting material.

We claim:

1. A process for the production of a high-purity diphenyl carbonate, the process comprising the steps of:
   (i) carrying out a transestrification reaction between a dialkyl carbonate and a phenol and/or a disproportionation reaction of an alkyl carbonate and/or a transesterification reaction between an alkyl phenyl carbonate and a phenol in the presence of a homogeneous catalyst, so as to form a reaction mixture containing a diphenyl carbonate;
   (ii) carrying out separation by distillation in a high boiling point material separating column A into a column top component $A_T$ containing the diphenyl carbonate and a column bottom component $A_B$ containing the catalyst
   (iii) carrying out separation by distillation of said column top component $A_T$ in a diphenyl carbonate purifying column B having a side cut outlet into a column top component $B_T$, a side cut component $B_S$ and a column bottom component $B_B$, said column top component $A_T$ introducing from the side cut outlet into the column B;
   wherein
   (a) said high boiling point material separating column A comprises a continuous multi-stage distillation column having a length $L_A$ (cm), an inside diameter $D_A$ (cm), and an internal with a number of stages $n_A$ thereinside, wherein $L_A$, $D_A$, and $n_A$ satisfy the following formulae (1) to (3);

$$800 \leq L_A \leq 3000 \tag{1}$$

$$100 \leq D_A \leq 1000 \tag{2}$$

$$20 \leq n_A \leq 100 \tag{3};$$

(b) said diphenyl carbonate purifying column B comprises a continuous multi-stage distillation column having a length $L_B$ (cm), an inside diameter $D_B$ (cm), an internal thereinside, an inlet B1 at a middle portion of the column, and a side cut outlet B2 between said inlet B1 and the column bottom, in which a number of stages of the internal above the inlet B1 is $n_1$, a number of stages $n_2$ of the internal between the inlet B1 and the side cut outlet B2 is $n_2$, a number of stages $n_3$ of the internals below the side cut outlet B2 is $n_3$, and a total number of stages is $n_B$ ($=n_1+n_2+n_3$), wherein $L_B$, $D_B$, $n_1$, $n_2$, $n_3$, and $n_B$ satisfy the following formulae (4) to (9);

$$1000 \leq L_B \leq 5000 \tag{4}$$

$$100 \leq D_B \leq 1000 \tag{5}$$

$$5 \leq n_1 \leq 20 \tag{6}$$

$$12 \leq n_2 \leq 40 \tag{7}$$

$$3 \leq n_3 \leq 15 \tag{8}$$

$$20 \leq n_B \leq 70 \tag{9}.$$

2. The process according to claim 1, wherein not less than 1 ton/hr of the high-purity diphenyl carbonate is obtained as the side cut component $B_S$.

3. The process according to claim 1 or 2, wherein $L_A$, $D_A$, and $n_A$ for said high boiling point material separating column A satisfy the following formulae: $1000 \leq L_A \leq 2500$, $200 \leq D_A \leq 600$, and $30 \leq n_A \leq 70$, respectively, $L_B$, $D_B$, $n_1$, $n_2$, $n_3$, and $n_B$ for said diphenyl carbonate purifying column B satisfy the following formulae: $1500 \leq L_B \leq 3000$, $150 \leq D_B \leq 500$, $7 \leq n_1 \leq 15$, $12 \leq n_2 \leq 30$, $3 \leq n_3 \leq 10$, and $25 \leq n_B \leq 55$, respectively, $T_A$ is in a range of from 190 to 240° C., $P_A$ is in a range of from 2000 to 15000 Pa, $T_B$ is in a range of from 190 to 240° C., and $P_B$ is in a range of from 2000 to 15000 Pa.

4. The process according to claim 1, wherein each of said high boiling point material separating column A and said diphenyl carbonate purifying column B is a distillation column having a tray and/or a packing as said internal.

5. The process according to claim 4, wherein said internal of each of said high boiling point material separating column A and said diphenyl carbonate purifying column B is a packing.

6. The process according to claim 5, wherein said packing is structured packing.

* * * * *